US009970877B2

(12) United States Patent
Ewing et al.

(10) Patent No.: US 9,970,877 B2
(45) Date of Patent: May 15, 2018

(54) SERS DETECTION SYSTEM FOR CHEMICAL PARTICULATES AND LOW VAPOR PRESSURE CHEMICALS

(71) Applicants: Kenneth J. Ewing, Edgewood, MD (US); Jasbinder S. Sanghera, Ashburn, VA (US)

(72) Inventors: Kenneth J. Ewing, Edgewood, MD (US); Jasbinder S. Sanghera, Ashburn, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 251 days.

(21) Appl. No.: 14/207,724

(22) Filed: Mar. 13, 2014

(65) Prior Publication Data
US 2016/0161412 A1    Jun. 9, 2016

Related U.S. Application Data

(60) Provisional application No. 61/778,689, filed on Mar. 13, 2013.

(51) Int. Cl.
*G01N 21/65*      (2006.01)
*G01N 1/40*       (2006.01)

(52) U.S. Cl.
CPC ........... *G01N 21/658* (2013.01); *G01N 1/40* (2013.01); *G01N 2001/4027* (2013.01)

(58) Field of Classification Search
CPC . G01N 21/658; G01N 1/40; G01N 2001/4027
See application file for complete search history.

(56) References Cited

U.S. PATENT DOCUMENTS

| | | | | |
|---|---|---|---|---|
| 7,116,416 B1* | 10/2006 | Boss | .................. | B82Y 15/00 356/301 |
| 2002/0148305 A1* | 10/2002 | Danylewych-May | ... | G01N 1/02 73/863.21 |
| 2006/0286606 A1* | 12/2006 | Oliver | .................. | B01L 9/54 435/7.1 |
| 2007/0056388 A1* | 3/2007 | Henry | .................. | G01N 1/24 73/863.12 |
| 2007/0254377 A1* | 11/2007 | Li | .................. | G01N 21/658 436/171 |

(Continued)

OTHER PUBLICATIONS

Assemblies of silver nanocubes for highly sensitive SERS chemical vapor detection, Kodiyath et al. J. Mater. Chem. A, 2013, 1, 2777-2788.*

*Primary Examiner* — Dominic J Bologna
(74) *Attorney, Agent, or Firm* — US Naval Research Laboratory; Dawn C. Russell

(57) ABSTRACT

A method for detecting chemical aerosols and particulates on a surface by contacting a sample with a Surface Enhanced Raman Spectroscopy (SERS) substrate where the sample is an aerosol or a particulate on a surface, encapsulating the SERS substrate with the sample, heating the encapsulated sample so it vaporizes inside the encapsulation, cooling the vaporized sample so it deposits onto the SERS substrate, and irradiating the SERS substrate to collect a SERS spectrum of the sample. Also disclosed is the related system for detecting chemical aerosols and particulates on a surface.

8 Claims, 2 Drawing Sheets

(56) References Cited

U.S. PATENT DOCUMENTS

2010/0321684 A1* 12/2010 Bratkovski .......... G01N 21/658
　　　　　　　　　　　　　　　　　　356/301
2011/0271738 A1* 11/2011 McGill ................ G01N 21/64
　　　　　　　　　　　　　　　　　　73/23.41

* cited by examiner

SERS DETECTION SYSTEM FOR CHEMICAL PARTICULATES AND LOW VAPOR PRESSURE CHEMICALS

PRIORITY CLAIM

The present application is a non-provisional application claiming the benefit of U.S. Provisional Application No. 61/778,689, filed on Mar. 13, 2013 by Kenneth J Ewing et al., entitled "SERS Detection System for Chemical Particulates and Low Vapor Pressure Chemicals," the entire contents of which is incorporated herein by reference.

BACKGROUND OF THE INVENTION

Field of the Invention

The present invention relates generally to Surface Enhanced Raman Spectroscopy (SERS) detectors and, more specifically, to SERS systems capable of detecting either aerosols or particulates on surfaces.

Description of the Prior Art

Low vapor pressure toxic chemicals are a recognized threat by both military and Homeland Security agencies. These agents exhibit vapor pressures on the order of $10^{-6}$ to $10^{-8}$ torr, can exist as either liquid droplets or solid particulates, and present both an inhalation threat as an aerosol and a contact threat as surface particulates/droplets. Because of their extremely low vapor pressures, these materials cannot be detected using state-of-the-art chemical agent detectors which all require the sample to be in the vapor phase for detection. Therefore, there exists a need for the capability to collect and detect the presence of these toxic aerosols and particulates on surfaces in real time. Such a system can be used as a screening device prior to a more in-depth analysis of the collected chemical aerosol/particulate, or liquid droplet.

Surface Enhanced Raman Spectroscopy (SERS) has been studied for the past 30+ years and has been demonstrated to significantly enhance the Raman cross section of molecules adsorbed to the SERS surface. There has been a large effort in developing new SERS substrates as well as understanding the mechanism of the enhancement. The SERS enhancement is primarily due to the electric field generated by illuminating the gold or silver nanostructures on the surface with a laser. The electric field is generated by the excited plasmons in the metal which, when focused in a small area, give rise to a very large electric field. The SERS enhancement is proportional to the square of the electric field and SERS studies have successfully demonstrated single molecule detection using SERS. Therefore, SERS is an extraordinarily sensitive technique and, because it reports vibrational spectroscopic information of a target, it is also highly selective.

However, sensors based on the SERS effect are not currently in use because the common sampling approaches require the dissolution of samples in an appropriate solvent followed by spotting the solution onto the SERS substrate and allowing the sample to dry. Recent efforts at producing SERS substrates within a multi-capillary environment have enabled the measurement of chemical vapors; however, this approach is not applicable for detection of chemical particulates or low vapor pressure materials.

BRIEF SUMMARY OF THE INVENTION

The aforementioned problems are overcome in the present invention which provides a method for detecting chemical aerosols and particulates on a surface by contacting a sample with a Surface Enhanced Raman Spectroscopy (SERS) substrate where the sample is an aerosol or a particulate on a surface, encapsulating the SERS substrate with the sample, heating the encapsulated sample so it vaporizes inside the encapsulation, cooling the vaporized sample so it deposits onto the SERS substrate, and irradiating the SERS substrate to collect a SERS spectrum of the sample. Also disclosed is the related system for detecting chemical aerosols and particulates on a surface.

The purpose of the present invention is to use SERS to enable collection and real time detection of chemical aerosols or particulates on surfaces, such as Low Vapor Pressure (LVP) chemicals, non-traditional chemical agents, and novel chemical materials with minimal vapor pressure. To date there are no SERS systems capable of detecting either aerosols or particulates on surfaces. This invention enables the detection of trace levels of chemical aerosols and particulates on surfaces as well as aerosolized chemicals using SERS.

These and other features and advantages of the invention, as well as the invention itself, will become better understood by reference to the following detailed description, appended claims, and accompanying drawings.

DETAILED DESCRIPTION OF THE INVENTION

Figure 1:
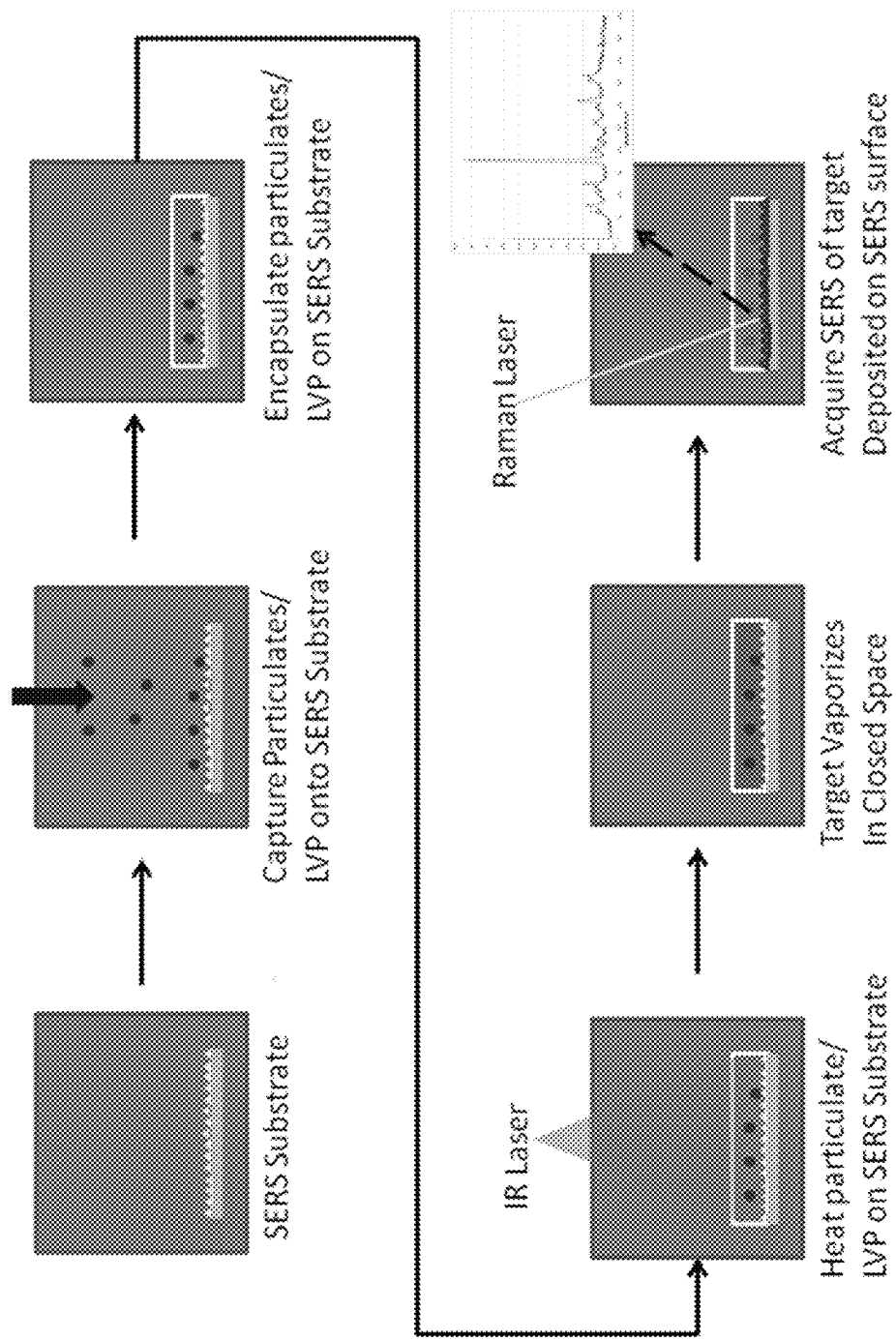
FIG. 1 shows the operation of an encapsulated Surface Enhanced Raman System for detection of chemical particulates/LVP chemicals.
Figure 2:
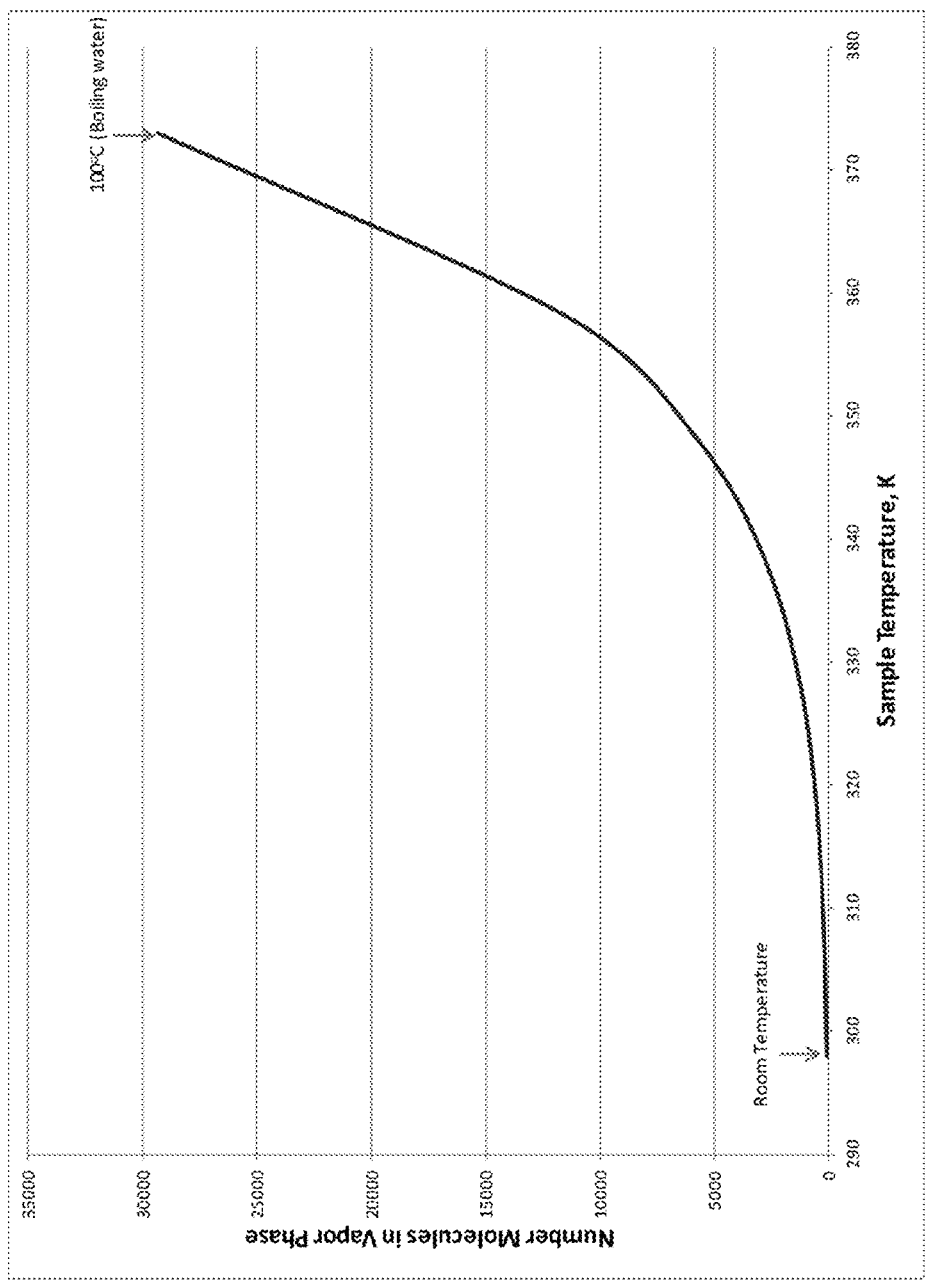
FIG. 2 shows a plot of the number of VX molecules vaporized in SERS encapsulated space for a 10 mm VX droplet versus the sample temperature.

The present invention is designed to enable rapid collection and analysis of chemical particulates from both an aerosol source and on environmental surfaces using Encapsulated Surface Enhanced Raman (E-SERS). The operation of the E-SERS system is diagrammed in FIG. 1. First the particulate/low vapor pressure material is collected onto the SERS substrate either by impacting the aerosol onto the SERS surface or contact of the SERS surface with a contaminated surface. Then the SERS surface, with particulates/LVP chemical, is encapsulated effectively sealing the chemical particulate/LVP chemical in an extremely small volume on the SERS surface. Next the particulate/LVP chemical is heated either by direct IR heating, heating of the substrate, or using a specific wavelength of light to heat the chemical particulate/LVP chemical. When heated the chemical particulate/LVP chemical will volatilize into the very small space defined by the size of the sealed particulate. The volatized chemical will therefore have a very large local concentration and will then be deposited onto the SERS substrate. Because of the high local concentration of the volatilized chemical particulate/LVP chemical, any environmental interferents sorbed onto the surface will be displaced by the volatilized chemical particulate/LVP chemical. FIG. 2 shows the number of molecules of the low vapor pressure chemical agent VX in the encapsulated space as the temperature is increased. It is evident that when heating the sample to 398 K (100° C.), a significant number of VX molecules are vaporized and therefore available for deposition onto the SERS substrate and subsequent detection via SERS. After the sample is vaporized, the heat is turned off, and the sample is cooled allowing the vaporized sample to deposit onto the SERS surface. Now the surface can be irradiated using a laser, and the SERS spectrum of the chemical particulate/LVP chemical can be collected.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method for detecting chemical aerosols and particulates on a surface, comprising:
    contacting a sample with a surface of a Surface Enhanced Raman Spectroscopy (SERS) substrate, wherein the sample comprises an aerosol, a particulate on a surface, or any combination thereof;
    encapsulating said sample within a closed space on the SERS substrate;
    heating the encapsulated sample wherein the sample vaporizes inside the closed space;
    cooling the vaporized sample within said closed space, wherein the vaporized sample is deposited onto the SERS substrate; and
    irradiating the SERS substrate within said closed space to collect a SERS spectrum of the sample.

2. The method of claim 1, wherein the sample comprises a low vapor pressure chemical.

3. The method of claim 2, wherein the low vapor pressure chemical has a vapor pressure of from $10^{-6}$ to $10^{-8}$ torr.

4. The method of claim 1, wherein the encapsulated sample is heated by direct IR heating, heating of the SERS substrate, or any combination thereof.

5. A system for detecting chemical aerosols and particulates on a surface, comprising:
    a sample comprising an aerosol, a particulate on a surface, or any combination thereof;
    a Surface Enhanced Raman Spectroscopy (SERS) substrate;
    a capsule for encapsulating the sample on the SERS substrate;
    means for heating the encapsulated sample to vaporize the sample inside the capsule;
    means for cooling the vaporized sample within said capsule so that the vaporized sample is deposited onto the SERS substrate; and
    a laser to irradiate the SERS substrate within said capsule to collect a SERS spectrum of the sample.

6. The system of claim 5, wherein the sample comprises a low vapor pressure chemical.

7. The system of claim 6, wherein the low vapor pressure chemical has a vapor pressure of from $10^{-6}$ to $10^{-8}$ torr.

8. The system of claim 5, wherein the encapsulated sample is heated by direct IR heating, heating of the SERS substrate, or any combination thereof.

* * * * *